United States Patent [19]
Morgan

[11] Patent Number: 5,466,244
[45] Date of Patent: Nov. 14, 1995

[54] DEFIBRILLATOR ELECTRODE SYSTEM

[75] Inventor: Carlton B. Morgan, Bainbridge Island, Wash.

[73] Assignee: Heartstream, Inc., Seattle, Wash.

[21] Appl. No.: 63,759

[22] Filed: May 18, 1993

[51] Int. Cl.⁶ ........................................ A61N 1/04
[52] U.S. Cl. .................. 607/5; 607/152; 128/640
[58] Field of Search ...................... 128/639–641; 607/5, 115, 142, 145, 148–150, 152, 36, 37

[56] References Cited

U.S. PATENT DOCUMENTS

| | | | |
|---|---|---|---|
| 2,632,447 | 3/1953 | Dobes | 607/152 |
| 2,943,628 | 7/1960 | Howell | 128/640 |
| 4,353,372 | 10/1982 | Ayer . | |
| 4,365,634 | 12/1982 | Bare et al. | 128/640 |
| 4,442,315 | 4/1984 | Segawa . | |
| 4,539,995 | 9/1985 | Segawa . | |
| 4,543,958 | 10/1985 | Cartmell . | |
| 4,583,549 | 4/1986 | Manoli . | |
| 4,838,273 | 6/1989 | Cartmell | 128/640 |
| 4,852,572 | 8/1989 | Nakahashi et al. . | |
| 4,957,109 | 9/1990 | Groeger et al. . | |
| 5,080,099 | 1/1992 | Way et al. . | |
| 5,148,805 | 9/1992 | Scharnberg | 128/640 X |
| 5,168,875 | 12/1992 | Mitchiner . | |
| 5,184,620 | 2/1993 | Cudahy et al. . | |
| 5,191,886 | 3/1993 | Paeth et al. . | |
| 5,341,806 | 8/1994 | Gadsby et al. | 128/640 |

FOREIGN PATENT DOCUMENTS

| | | | |
|---|---|---|---|
| 0353341 | 2/1990 | European Pat. Off. | 607/142 |

*Primary Examiner*—William E. Kamm
*Assistant Examiner*—Jeffrey R. Jastrzab
*Attorney, Agent, or Firm*—Morrison & Foerster

[57] ABSTRACT

A defibrillator electrode system. In the preferred embodiments, each electrode and the conductor leading to the instrument (such as the defibrillator or ECG monitor) is mounted on the same flexible substrate. In one two-electrode system embodiment, each electrode-conductor pair is mounted on a separate flexible substrate, and the two substrates are mounted in a retainer. In another preferred two-electrode system embodiment, the two electrode-conductor pairs are mounted on the same flexible substrate. In both embodiments, the retainer attaches to the instrument and provides the electrical connection between the conductors and the instrument. Conductive gel covers the electrodes in the preferred embodiments, and an adhesive surrounds the electrodes. The flexible substrate is provided with a release coating in appropriate spots. In their undeployed storage positions, the electrodes' conductive gel portions and adhesive portions lie against the release coating. During deployment, the conductive gel and adhesive peel away from the release coating. This arrangement minimizes the number of steps required in deploying defibrillator electrodes and preserves the integrity of the electrodes during storage.

28 Claims, 6 Drawing Sheets

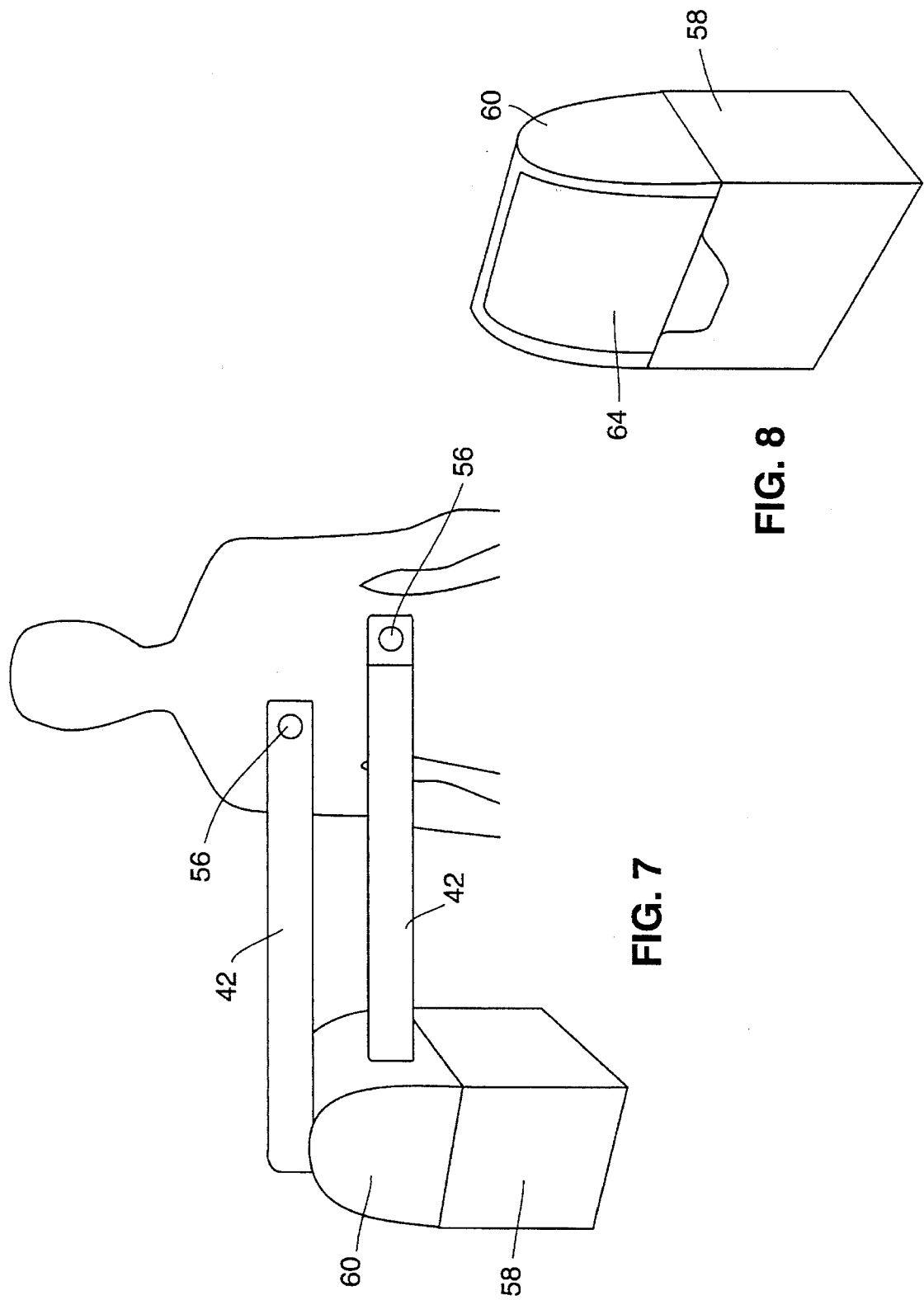

DEFIBRILLATOR ELECTRODE SYSTEM

BACKGROUND OF THE INVENTION

This invention relates generally to medical electrode systems and, in particular, to a disposable defibrillator electrode system.

Defibrillators apply voltage pulses to a patient's heart in response to a life-threatening condition such as cardiac arrest. External defibrillators deliver the voltage pulse through a pair of electrodes placed on the patient's chest or back by the attending medical personnel. The primary components of a defibrillator system are the defibrillator, which provides the voltage pulse, and the electrodes, which deliver the voltage pulse to the patient.

Prior art external defibrillator electrodes consist of a paddle having an electrode face electrically connected to the defibrillator by a cable. A conductive gel on the electrode face lowers the electrical resistance between the electrode and the patient. Disposable defibrillator electrodes are typically packaged with the gel pre-applied to the electrode face. Adhesive holds the electrodes in place on the patient. With standard reusable electrodes, on the other hand, the user must apply the gel before placing the electrodes on the patient. Handles on the back side of the electrode paddles enable the user to place the electrodes at the desired sites on the patient to hold the electrodes against the patient's skin.

SUMMARY OF THE INVENTION

One drawback of prior art defibrillator systems is the number of steps required to deploy the electrodes. Because defibrillators are used primarily in emergency situations, deployment and operation of defibrillator electrodes should be quick, easy and reliable. Prior art disposable defibrillator electrodes, however, require the following steps for deployment prior to delivery of the defibrillation pulse: connection of a cable to the defibrillator; deploying the cable, which often requires untangling of the cable; removal of the electrodes from their package; attachment of the electrodes to the cable; removal of the release liner covering the conductive gel over each electrode face and any adhesive surrounding the electrode; visual inspection of each electrode to determine whether it is usable; and application of the electrodes to the patient. Each of these steps takes time, and time is of the essence when trying to save a patient's life.

Furthermore, if a visual inspection or actual defibrillation attempt shows that either electrode is inoperative due to deterioration of the conductive gel, a broken conductor in the cable, a broken connection between the cable and the electrode, etc., then the deployment process must begin again, wasting even more time. What is needed, therefore, is a defibrillator electrode system requiring fewer steps for deployment and preserving the integrity of the electrodes prior to use.

This invention provides a defibrillator electrode system that is reliable and easy to use. In the preferred embodiments, each electrode and the conductor leading to the instrument (such as the defibrillator or ECG monitor) is mounted on the same flexible substrate. In one two-electrode system embodiment, each electrode-conductor pair is mounted on a separate flexible substrate, and the two substrates are mounted in a retainer. In another preferred two-electrode system embodiment, the two electrode-conductor pairs are mounted on the same flexible substrate. In both embodiments, the retainer attaches to the instrument and provides the electrical connection between the conductors and the instrument.

Conductive gel covers the electrodes in the preferred embodiments, and an adhesive surrounds the electrodes. The flexible substrate is provided with a release coating in appropriate spots. In their undeployed storage positions, the electrodes' conductive gel portions and adhesive portions lie against the release coating. During deployment, the conductive gel and adhesive peel away from the release coating. This arrangement minimizes the number of steps required in deploying defibrillator electrodes and preserves the integrity of the electrodes during storage.

The invention is explained in more detail below with reference to the drawings.

BRIEF DESCRIPTION OF THE DRAWINGS

FIG. 7 shows the electrode system of the preferred embodiment fully deployed and placed on the patient.

FIG. 8 shows a protective covering for the electrode system according to another aspect of the invention.

DETAILED DESCRIPTION OF THE PREFERRED EMBODIMENT

Figure 1:
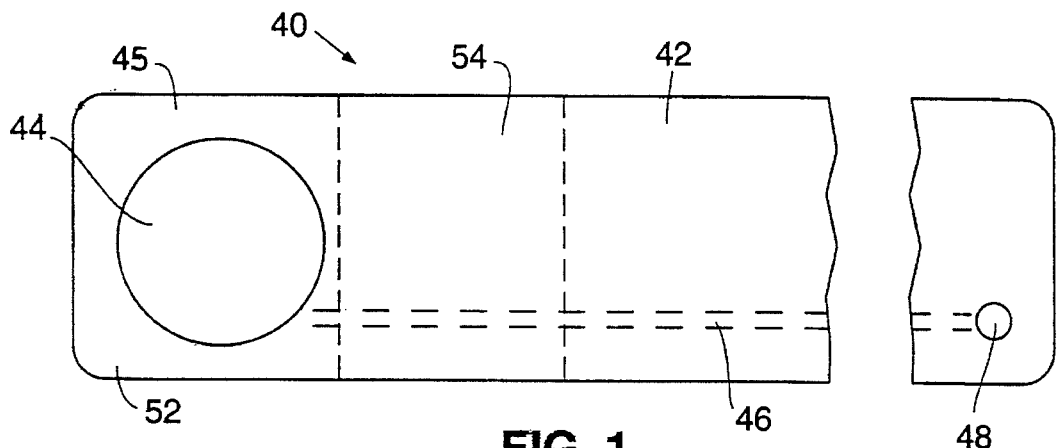
FIG. 1 shows an electrode according to a preferred embodiment of this invention.
Figure 2:
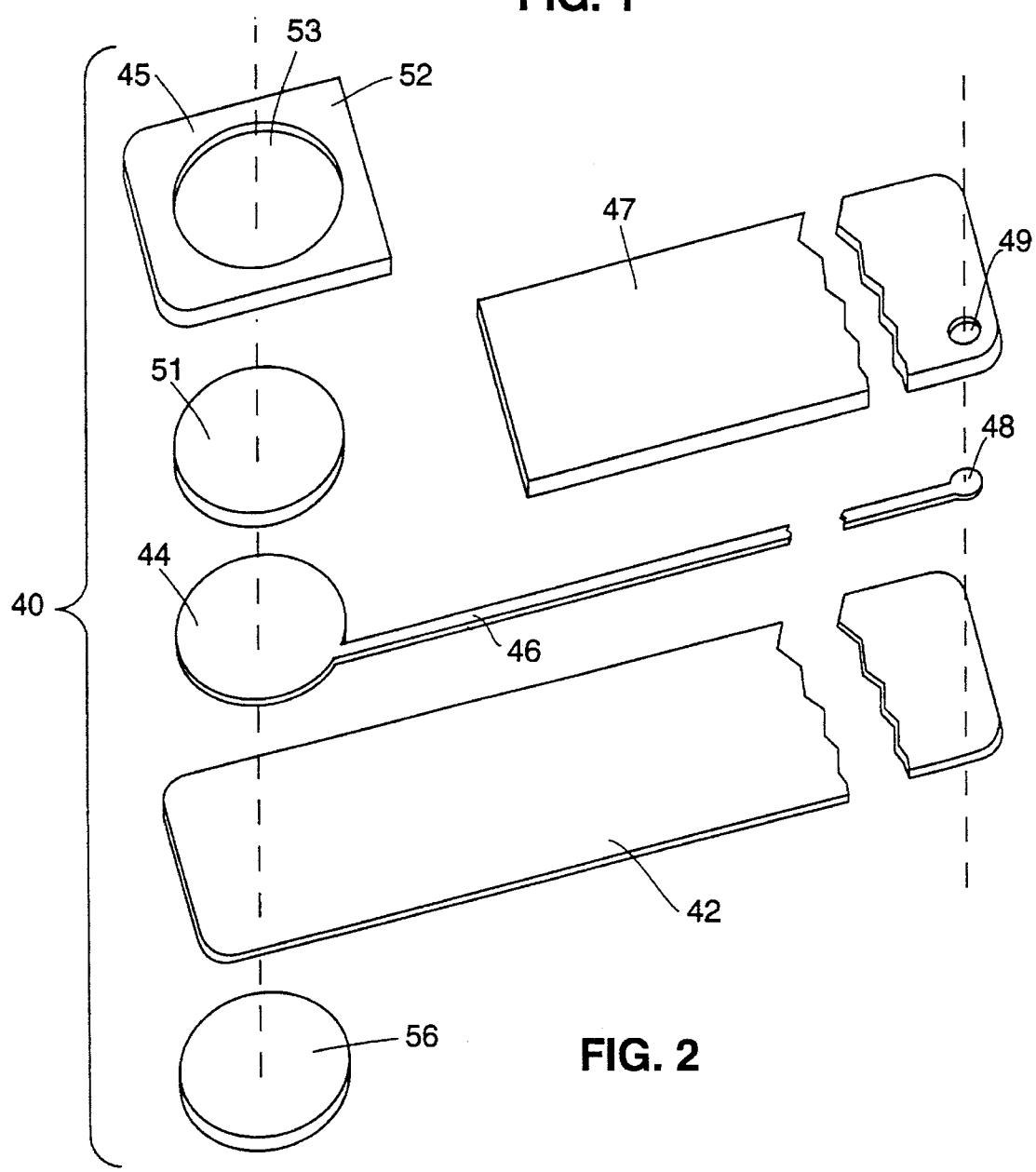
FIG. 2 is an exploded view of the electrode of FIG. 1.

FIGS. 1–8 show an electrode apparatus according to a preferred embodiment of this invention. As shown in FIGS. 1 and 2, the electrode apparatus 40 has a relatively stiff electrode body 45 attached to a flexible substrate 42 with a medical grade adhesive. In this embodiment, substrate 42 is a polymer such as polyester or Kapton, approximately 3 mils thick. The length of substrate 42 depends on the requirements of the application. Electrode body 45 is preferably made from a light-weight, closed-cell foam approximately 25 mils thick.

An electrode disk 44 is disposed within electrode body 45. Electrode disk 44 is preferably a circular piece of metal foil, such as 3 mil tin, approximately 80 $cm^2$ in area, attached to substrate 42 with a suitable medical grade adhesive. Electrode disk 44 is covered with a layer of conductive gel 51 in a known manner. The thickness of gel layer 51 is 25 mils to make its top surface even with the surrounding electrode body surface. Medical grade adhesive is disposed in adhesive area 52 on the top surface of electrode body 45 surrounding the opening 53 for electrode disk 44.

A conductor 46 and an electrical attachment pad 48 are formed on, or attached to, flexible substrate 42. Conductor 46 and electrical attachment pad 48 are preferably 3 mil tin foil formed integrally with electrode disk 44 and attached to substrate 42 with adhesive. An insulating cover 47 is disposed over substrate 42 and conductor 46 and attached to substrate 42 with adhesive. Cover 47 has a silicon release coating on its top side. An opening 49 is formed in cover 47 so that attachment pad 48 can make electrical contact with a connector, as described below.

Figure 3:
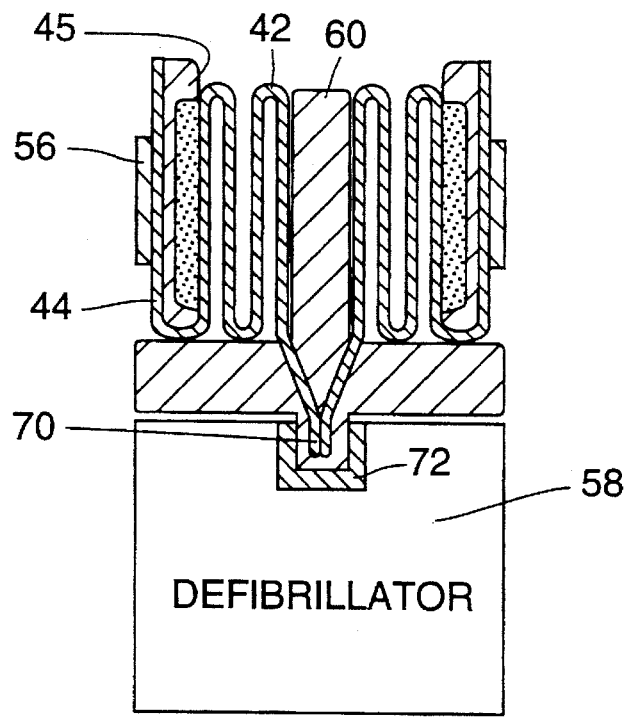
FIG. 3 is a side cross-sectional view of an electrode system according to a preferred embodiment, prior to deployment.
Figure 4:
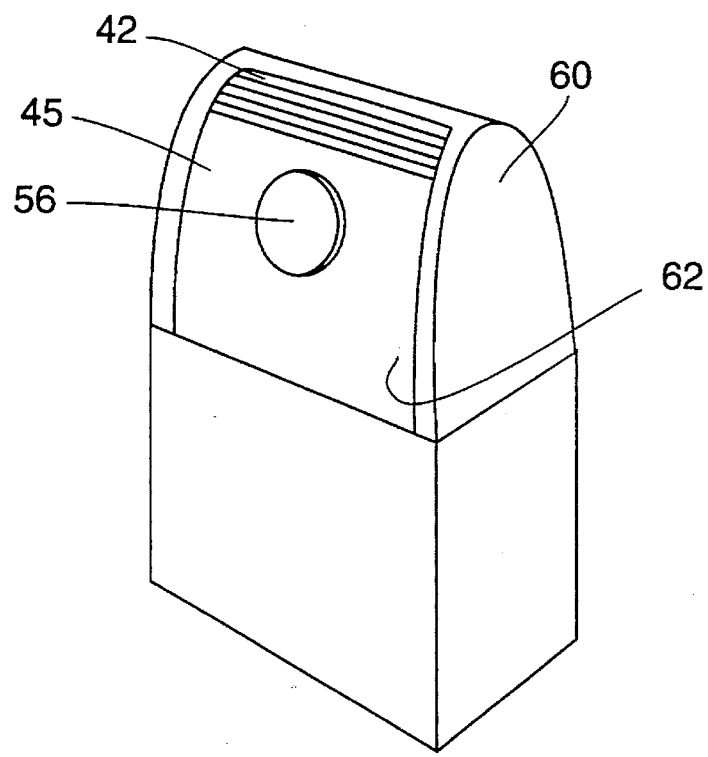
FIG. 4 is a perspective view of the electrode system of FIG. 3.

In FIGS. 3–7, a pair of the electrodes shown in FIGS. 1 and 2 are mounted in a retainer for use with a defibrillator system. FIGS. 3 and 4 show the electrodes in a predeployment storage position. In this position, the flexible substrate 42 of each electrode is folded in an accordion fashion and placed in retainer 60.

Figure 5:
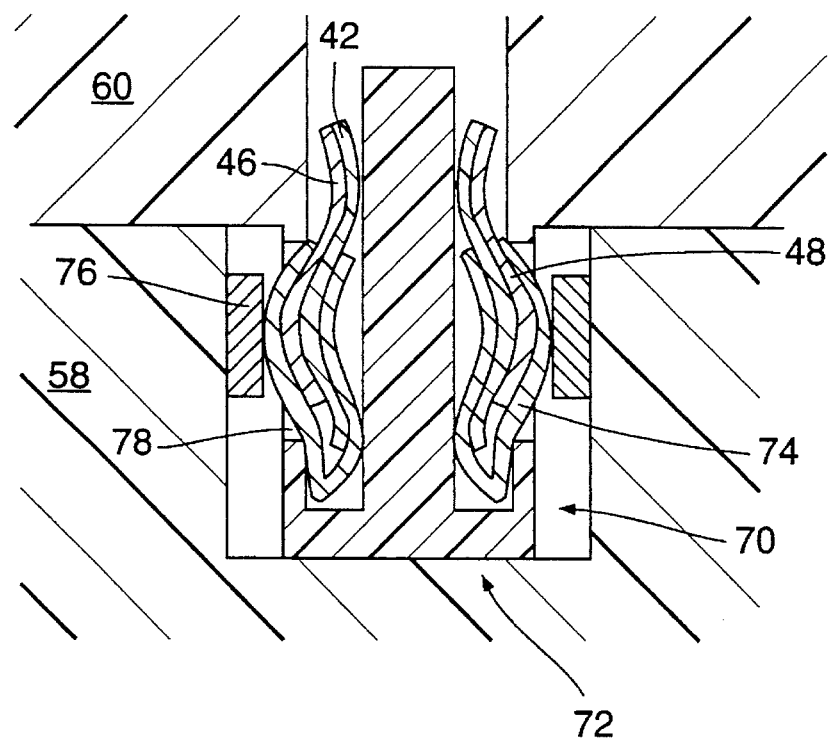
FIG. 5 is a cross-sectional view of a connector between an electrode system and an instrument.

The portion of substrate 42 on which the attachment pad 48 is located extends into a retainer connector area 70 for electrical attachment to a corresponding connector 72 on the defibrillator 58. FIG. 5 shows the details of one embodiment of the connectors. A metal crimp 74 at the end of substrate 42 makes electrical contact with attachment pad 48. The crimp 74 partially extends through an opening 78 in the connector portion 70 of retainer 60. When the retainer connector portion is inserted into the connector portion of the defibrillator 58, crimp 74 makes electrical contact with defibrillator contact 76. The resilient action of the crimps 74 also provide the mechanical attachment of retainer 60 to defibrillator 58. Alternatively, other known mechanical attachment mechanisms may be used to fasten retainer 60 to defibrillator 58. The contacts 76 for each electrode are connected to the defibrillator electronics in a known manner.

In the folded position, electrode disk 44, the conductive gel covering the electrode disk, and the adhesive surrounding the electrode disk lie against an area 54 on the top surface of substrate 42. The top surface of substrate 42 is coated with a suitable release coating such as silicon in at least release area 54. The release coating enables electrode disk 44, its gel coating and the adhesive to peel away from substrate 42 during deployment of the electrode, as discussed below. The covering action of the substrate over the conductive gel also helps keep the conductive gel from drying out during storage. A handle 56 attached to the back side of electrode body 45 lies in position in which it can be grasped by a user during deployment of the electrodes.

Figure 6:
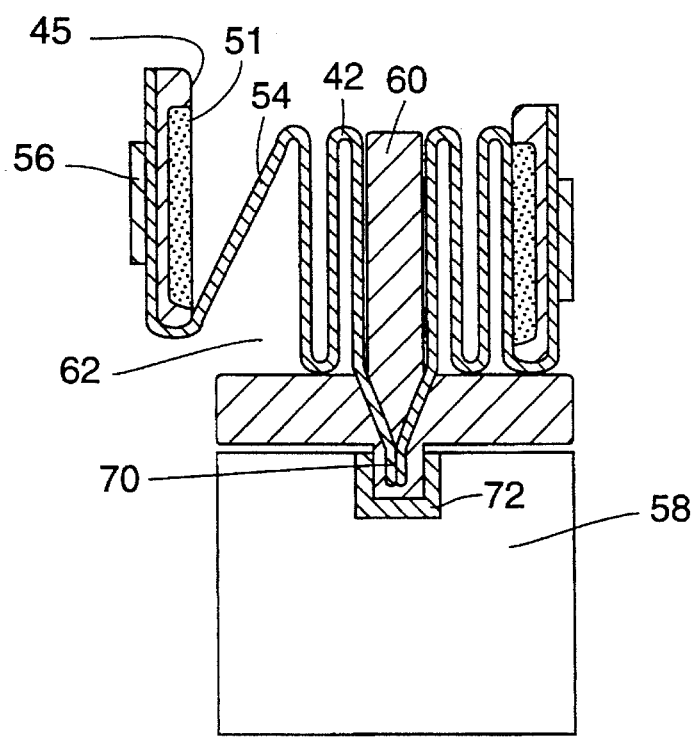
FIG. 6 is a side cross-sectional view of the electrode system of this invention with one electrode partially deployed.

FIGS. 6 and 7 demonstrate deployment and placement of the electrodes on the patient. As shown in FIG. 4, the user pulls electrode body 45 up and out of retainer 60 through openings 62 by grasping handle 56. As it moves out of the retainer, the electrode disk 44 and its conductive gel layer 51 peel away from substrate surface 42. The pair of electrodes in retainer 60 may be extended as far as needed to reach the appropriate sites on the patient, as shown in FIG. 7. The conductors 46 and attachment pads 48 on the substrates provide the electrical connection between the electrodes and the defibrillator for delivery of the defibrillating voltage pulse and/or for monitoring of the electrical activity of the patient's heart. After use, the retainer and the pair of electrodes it houses can be discarded and replaced with a new electrode set.

It may be necessary to store the electrodes for an extended period prior to their deployment and use. FIG. 8 shows a possible protective covering for preserving the integrity of the electrodes by, for example, preventing the conductive gel from drying out. The openings 62 of retainer 60 are covered with a flap 64. The flap may be formed from foil-backed paper or plastic, such as Tyvek. Flap 64 is peeled back from the retainer openings just prior to deployment of the electrodes.

Figure 9:
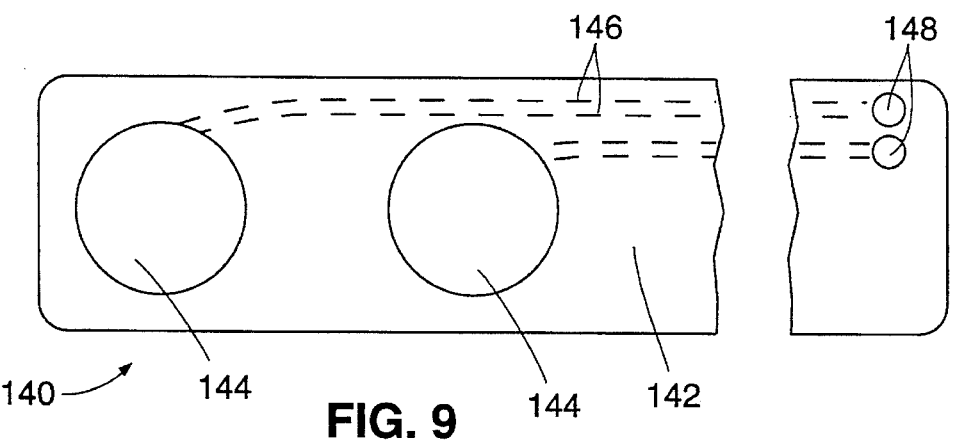
FIG. 9 shows an alternative embodiment of the electrode system of this invention.
Figure 10:
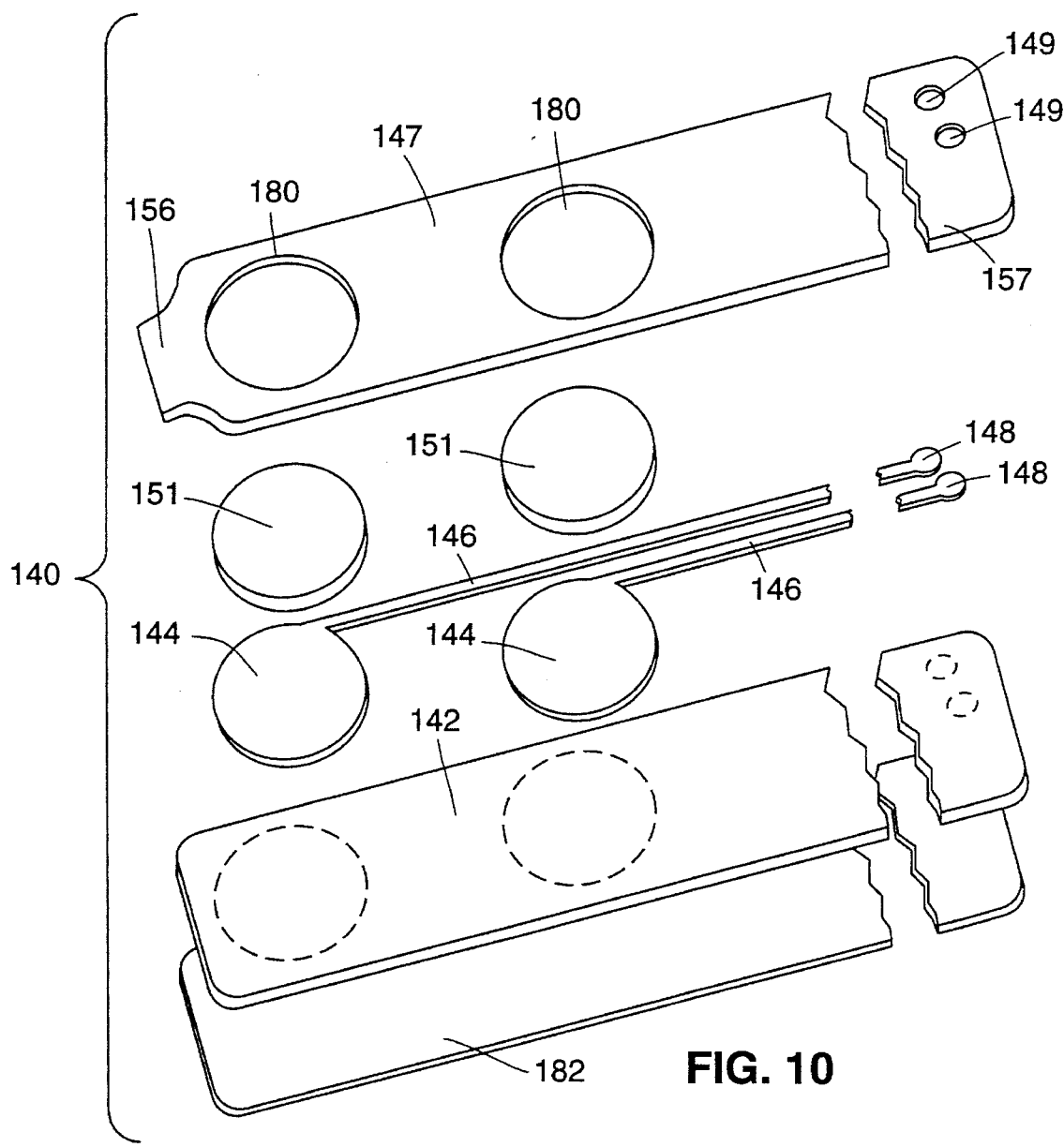
FIG. 10 is an exploded view of the electrode system of FIG. 9.

FIGS. 9–12 show an alternative embodiment of this invention. As shown in FIGS. 9 and 10, the electrode apparatus 140 has a flexible body or substrate 142, preferably formed from 1/16" closed cell foam. A backing layer 182 is attached to the underside of substrate 142 with a medical grade adhesive. Backing layer 182 may be formed from Tyvek or any other suitable material. The underside of backing layer 182 is coated with a silicon release material.

A pair of electrodes 144 are adhesively attached to the top of substrate 142. Conductors 146 lead from electrodes 144 to attachment pads 148. Each set of electrode, conductor and attachment pad is preferably formed from a single piece of tin metal foil 3 mils thick. The surface area of each electrode is preferably 80 cm$^2$. A layer of conductive gel 151 covers each electrode. The thickness of the conductive gel layer is preferably 25 mils.

An insulating cover 147 is attached to the top side of substrate 142 with medical grade adhesive. Cover 147 has openings 180 for the electrodes and openings 149 for the attachment pads. Openings 180 have diameters slightly smaller than the diameters of their respective electrodes, and openings 149 have diameters slightly smaller than the diameters of their respective attachment pads. Medical grade adhesive covers all of the top surface of cover 147 except for handle area 156 and connector area 157 for attachment of the electrode apparatus to a patient.

Figure 12:
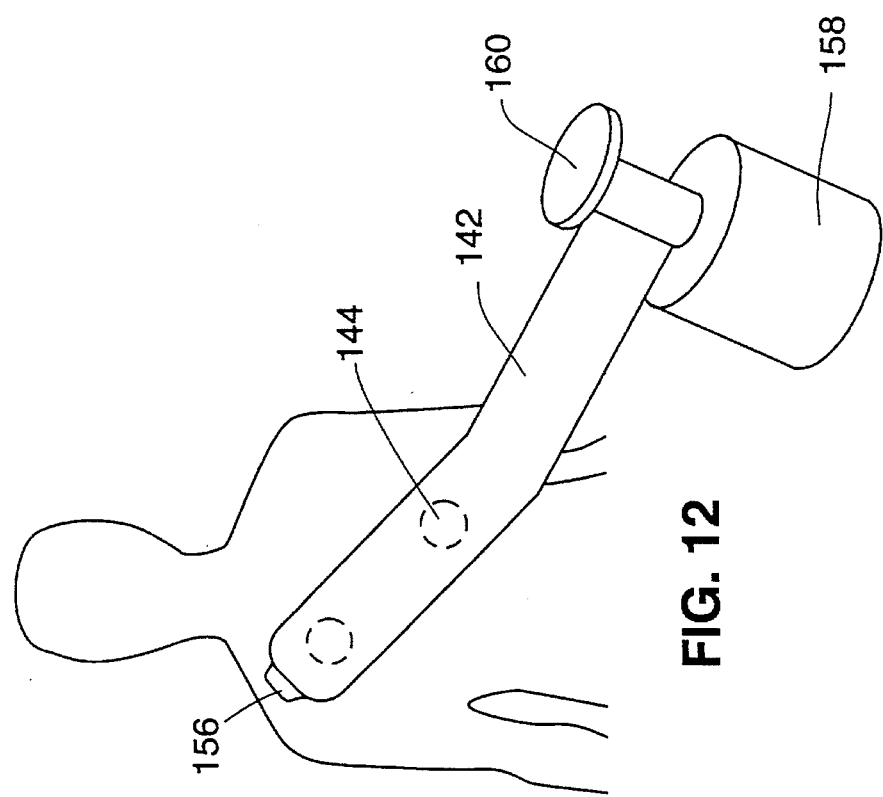
FIG. 12 shows the electrode system of this embodiment fully deployed and placed on the patient.
Figure 11:
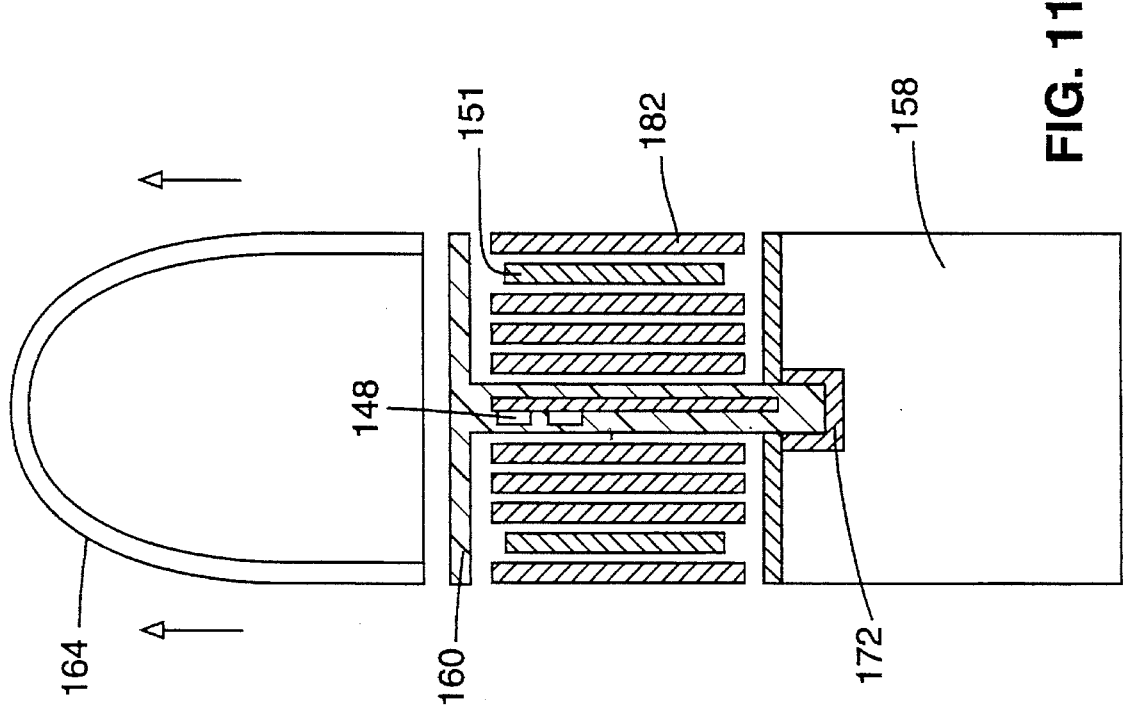
FIG. 11 is a side cross-sectional view of the embodiment of FIG. 9, prior to deployment.

FIGS. 11 and 12 show the electrode apparatus of this embodiment mounted in a retainer. As seen in FIG. 11, prior to deployment, the electrode apparatus is wound around a spool-shaped retainer 160 mounted on top of a defibrillator 158. The portion of the electrode apparatus on which the attachment pads 148 are located extend into the center of the retainer spool where they make electrical connection with conductors (not shown) that connect to the defibrillator connector 172. A protective cover 164 may be kept over retainer spool 160 until the electrodes are to be deployed.

In the undeployed position shown in FIG. 11, the conductive gel layers 151 and the adhesive coating on cover layer 147 face the inward toward the center of the retainer spool and the release coating on the underside of backing layer 182 faces outward from the center. Thus, when the electrode apparatus is wound about itself, the conductive gel layers 151 and the adhesive coating on the cover layer lie against the silicon release coating of the backing layer 182.

To deploy the electrode apparatus of this embodiment, the protective cover 164 is removed, and the electrode apparatus is unwound from retainer spool 160 by pulling on handle or tab 156. The release coating on backing layer 182 permits the conductive gel layers 151 and the adhesive on cover layer 147 to peel away. The electrode apparatus is then applied to the patient as shown in FIG. 12.

The electrode apparatus and retainer spool remain attached to the defibrillator during use. The conductors 146 and attachment pads 148 provide the electrical connection between the electrodes 144 and the defibrillator for delivery of the defibrillating voltage pulse and/or for monitoring of the electrical activity of the patient's heart. After use, the retainer spool and the electrode apparatus it houses can be discarded and replaced with a new electrode set.

Other configurations are possible without departing from the scope of the invention. For example, other shapes of the retainer and the protective covering may be used. In addition, a battery may be disposed in the electrode retainer to provide the power to the defibrillator. On the other hand, the retainer may be omitted altogether and the electrodes attached directly to the defibrillator or other instrument.

The electrically conductive traces on the flexible substrate may be replaced in whole or in part by wires or other conductors. Other materials and dimensions may be employed. Finally, while this invention has been described in the context of defibrillators and defibrillator electrodes, it should be understood that the invention applies to medical electrodes used with other instruments, such as an ECG monitor.

Other modifications will be apparent to those skilled in the art.

What is claimed is:

1. A medical electrode system comprising:
   a flexible substrate;
   a conductor disposed on the substrate;
   an electrode disposed on the substrate and electrically connected to the conductor;
   the substrate comprising an adhesive area and a release area permanently attached to the substrate and adhered to the adhesive area,
   the electrode being disposed against the release area.

2. The medical electrode system of claim 1 wherein the substrate is formed from a polymer.

3. The medical electrode system of claim 2 wherein the wherein the substrate is shaped substantially as a rectangle.

4. The medical electrode system of claim 2 wherein the conductor is formed from metal foil attached to the substrate.

5. The medical electrode system of claim 1 wherein the substrate has a first surface and a second surface, the adhesive area being disposed on the first surface of the substrate and the release area being disposed on the first surface of the substrate.

6. The medical electrode system of claim 1 wherein the substrate has a first surface and a second surface, the adhesive area being disposed on the first surface of the substrate and the release area being disposed on the second surface of the substrate.

7. The medical electrode system of claim 1 further comprising a second conductor disposed on the substrate and a second electrode disposed on the substrate and electrically connected to the second conductor.

8. The medical electrode system of claim 7 further comprising a retainer, the substrate being housed in the retainer when the electrodes are in an undeployed position, the adhesive area being disposed against the release area when the electrodes are in said undeployed position.

9. The medical electrode system of claim 8 further comprising a connector electrically connected to each conductor.

10. The medical electrode system of claim 9 wherein the retainer comprises a connector area in which the connectors are disposed.

11. The medical electrode system of claim 8 further comprising a protective cover enclosing the substrate when the electrodes are in an undeployed position.

12. The medical electrode system of claim 1 further comprising a retainer, the substrate being housed in the retainer when the electrode is in an undeployed position, the adhesive area being adhered to the release area when the electrode is in said undeployed position.

13. The medical electrode system of claim 12 further comprising a second flexible substrate; a conductor disposed on the second substrate; an electrode electrically connected to the conductor on the second substrate; an adhesive area on the second substrate and a release area on the second substrate; the second substrate being housed in the retainer when the electrode on the second substrate is in an undeployed position, the adhesive area on the second substrate being adhered to the release area on the second substrate when the electrode on the second substrate is in said undeployed position.

14. The medical electrode system of claim 13 further comprising a protective cover enclosing the substrates within the retainer when the electrodes are in an undeployed position.

15. The medical electrode system of claim 41 further comprising a connector electrically connected to the conductor of each substrate.

16. The medical electrode system of claim 15 wherein the retainer comprises a connector area in which the connectors from the first and second substrate are disposed.

17. The medical electrode system of claim 1 wherein the adhesive area is adjacent the electrode.

18. The medical electrode system of claim 1 wherein the adhesive area surrounds the electrode.

19. The medical electrode system of claim 1 wherein the electrode comprises conductive gel.

20. The medical electrode system of claim 1 further comprising a connector electrically connected to the conductor.

21. The medical electrode system of claim 1 further comprising a release coating on the release area.

22. A method of deploying a medical electrode comprising the following steps:
   providing a substrate supporting an electrode; the substrate having an adhesive area; a conductor electrically connected to the electrode; the electrode and the substrate adhesive area being disposed against a second area of the substrate; and
   moving the electrode and the adhesive area away from the second area of the substrate.

23. The method of claim 22 wherein the moving step further comprises the step of extending the substrate from a first length to a second, longer length.

24. The method of claim 22 wherein the moving step comprises the step of moving the substrate from a wound position to an unwound position.

25. The method of claim 22 wherein the providing step further comprises the step of providing a retainer holding the electrode and the substrate in an undeployed position, the moving step comprising the step of moving the electrode and at least part of the substrate away from the retainer.

26. The method of claim 25 further comprising the step of electrically connecting the conductor to an instrument for sending electrical signals to, or receiving electrical signals from, the electrode.

27. The method of claim 26 wherein the retainer has a connector area electrically connected to the electrode through the conductor, the electrically connecting step comprising mating the connector area to a corresponding area on the instrument.

28. The method of claim 25 wherein the retainer has a protective cover, the method further comprising the step of removing the protective cover before the moving step.

* * * * *

UNITED STATES PATENT AND TRADEMARK OFFICE
CERTIFICATE OF CORRECTION

PATENT NO. : 5,466,244

DATED : November 14, 1995

INVENTOR(S) : Carlton B. Morgan

It is certified that error appears in the above-indentified patent and that said Letters Patent is hereby corrected as shown below:

In column 5, lines 27-28, after "wherein the" please delete "wherein the".

Signed and Sealed this

Fourteenth Day of May, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,466,244
DATED : November 14, 1995
INVENTOR(S) : Carlton B. Morgan It is certified that error appears in the above-indentified patent and that said Letters Patent is hereby corrected as shown below:

In Column 1, line 10, "arrest," should be —arrest.—.

In Column 4, line 43, after "face," please delete "the".

In Column 6, line 3 (claim 13), "substrate" should be —substrate;—.

In Column 6, line 15 (claim 15), "claim 41" should be —claim 13—.

In Column 6, line 20 (claim 16), "substrate" should be —substrates—.

Signed and Sealed this

Eighth Day of July, 1997

Attest:

BRUCE LEHMAN

*Attesting Officer*     *Commissioner of Patents and Trademarks*